United States Patent [19]
Cote et al.

[11] Patent Number: 5,879,143
[45] Date of Patent: Mar. 9, 1999

[54] RESERVOIR ENCLOSURE ADAPTORS AND METHODS

[75] Inventors: Steven Albert Cote, Stillwater; Thomas Lloyd Peterson; Brian Keith Sorensen, both of Shoreview, all of Minn.

[73] Assignee: SIMS Deltec, Inc., St. Paul, Minn.

[21] Appl. No.: 638,114

[22] Filed: Apr. 26, 1996

[51] Int. Cl.$^6$ .................................................. F04B 17/00
[52] U.S. Cl. ......................................... 417/474; 604/153
[58] Field of Search ............................. 417/474, 53, 12, 417/234, 360; 604/67, 153, 131, 132; 222/103, 93, 96; 128/DIG. 12

[56] References Cited

U.S. PATENT DOCUMENTS

| | | |
|---|---|---|
| 3,731,679 | 5/1973 | Wilhelmson et al. . |
| 4,398,908 | 8/1983 | Siposs . |
| 4,416,595 | 11/1983 | Cromie . |
| 4,559,038 | 12/1985 | Berg et al. . |
| 4,565,542 | 1/1986 | Berg . |
| 4,650,469 | 3/1987 | Berg et al. . |
| 4,657,486 | 4/1987 | Stempfle et al. . |
| 4,950,245 | 8/1990 | Brown et al. . |
| 5,011,378 | 4/1991 | Brown et al. . |
| 5,017,059 | 5/1991 | Davis . |
| 5,078,683 | 1/1992 | Sancoff et al. . |
| 5,165,874 | 11/1992 | Sancoff et al. . |
| 5,181,910 | 1/1993 | Scanlon . |
| 5,324,258 | 6/1994 | Rohrbough . |
| 5,330,431 | 7/1994 | Herskowitz ........................... 604/153 |
| 5,336,190 | 8/1994 | Moss et al. . |
| 5,342,313 | 8/1994 | Campbell et al. . |
| 5,567,119 | 10/1996 | Johnson ................................. 417/53 |

OTHER PUBLICATIONS

Exhibit A, Photographs of a lock box product by Pharmacia Deltec, pp. A1–A4.

Exhibit Supplemental A, CADD Enclosure brochure (Jan. 18, 1991).

Exhibit B, Photographs of a first pump product by C.R. Bard, Inc., pp. B1–B5.

Exhibit Supplemental B, Bard® Ambulatory PCA Infusion Pump Quick Reference Guide (Apr. 1990).

Exhibit Supplemental B–1, Patient Guide for the Bard® Ambulatory PCA Infusion Pump brochure, (undated).

Exhibit C, Photographs of a second pump product by C.R. Bard, Inc., pp. C1–C5.

Exhibit D, Photographs of a pump product by Patient Solutions, Inc., Med–Mate™, Model 1100, pp. D1–D2.

Exhibit Supplemental D, MedMate™ 1100 brochure (undated)(selected pages).

Exhibit E, Photographs of a pump product by Block Medical, Inc., a Hillenbrand Industry, Verifuse®, Model No. B001500, pp. E1–E5.

Exhibit Supplemental E, Verifuse® Lock Box Instructions (undated).

Exhibit Supplemental E–1, Verifuse® Ambulatory Infusion System Nurse Guide (®copyright 1991, 1993).

Exhibit Supplemental E–2, Verifuse® Ambulatory Infusion System Patient Guide (®copyright 1991, 1993).

(List continued on next page.)

*Primary Examiner*—Ismael Izaguirre
*Attorney, Agent, or Firm*—Merchant, Gould, Smith, Edell, Welter & Schmidt P.A.

[57] ABSTRACT

This invention relates to adaptors designed to secure an infusion-type pump to an enclosure for delivery of fluids, including medicaments, and the like to a patient in need of such treatment. The enclosure is of a type designed to house a fluid reservoir and conduit extending from the fluid reservoir to the infusion-type pump. The adaptor forms a substantially planar plate having a back face and a front face. The front face includes guides and a support plate to align the pump onto the adaptor. Securing grips are provided to secure the pump onto the adaptor. The adaptor has a back face to reversibly engage the enclosure.

21 Claims, 5 Drawing Sheets

OTHER PUBLICATIONS

Exhibit F, Photographs of a pump product by Medfusion, Inc., a Medex, Inc. Company, Infu–Med™, WalkMed™ 440 PIC, pp. F1–F4.

Exhibit Supplemental F, Medfusion Inc., WalkMed™ 410c, WalkMed™ 420i/c, WalkMed™ 430PCA, WalkMed™ 440PIC brochure (undated).

Exhibit Supplemental F–1, WalkMed® PCA brochure (®1993).

Exhibit G, Pharmacia Deltec brochure entitled "CADD® Pump Accessories," dated Apr. 1991.

Exhibit H, Pharmacia Deltec brochure entitled "Instructions for Use One Liter Pouch for Pharmacia Deltec–Ambulatory Infusion Pumps," dated Apr. 1989.

Exhibit I, Pharmacia Deltec brochure entitled "CAD–TPN™ Backpack Diagram," dated Oct. 1990.

Exhibit J, Pharmacia Deltec brochure entitled "50–/100–ml Dual Pump Pouch for use with Pharmacia Deltec Ambulatory Infusion Pumps and Accessories Instructions for Use," dated Sep. 1992.

RESERVOIR ENCLOSURE ADAPTORS AND METHODS

FIELD OF THE INVENTION

The present invention relates to infusion systems and methods utilizing enclosures for fluid reservoirs associated with ambulatory pumps for delivering fluid to a patient. In particular, this invention relates to reservoir enclosure adaptors and methods for mounting the pumps to the enclosures.

BACKGROUND OF THE INVENTION

Infusion systems are known in the art and these systems include a fluid reservoir, a pump for pumping fluid from the fluid reservoir to the patient, and a tubing from the fluid reservoir to the pump and from the pump to the patient for transporting the fluid. Typically the fluid reservoir is a flexible bag made from a polymeric material or a syringe, and the pump is an infusion-style pump designed to deliver a premeasured fluid drug dose at a given rate to the patient in need of the drug.

U.S. patent application Ser. Nos. 08/145,371 now U.S. Pat. No. 5,540,561 and 08/388,200 now U.S. Pat. No. 5,567,119 disclose enclosure arrangements designed to protect fluid reservoirs, the disclosures of which are incorporated by reference. These enclosure arrangements include a chamber for receiving a fluid reservoir such as a flexible bag or a syringe. The enclosures each include an opening for accessing the chamber. The enclosures each further include a latch arrangement for mounting an ambulatory pump to the enclosure to protect the reservoir and tubing.

These enclosures have a number of advantages as enumerated in U.S. patent application Ser. Nos. 08/145,371 and 08/388,200. For example, flexible fluid reservoirs prepared from polymeric materials are capable of being punctured or torn by sharp objects. This can be a problem for patients who use the pumps outside the hospital or caregiver's office. This creates a particular problem when the fluid contained within the reservoir is irritating to the skin or where the fluid contains a controlled substance. Where the fluid contained within the reservoir is a controlled substance, such as a narcotic, the enclosures prevent the controlled substance from being withdrawn from the bag by a needle punctured through the polymeric material or the tubing.

Where the fluid reservoir is a syringe, the enclosures protect the syringe from manipulation and protects the tubing from the stresses that could be applied to it if the syringe and its tubing where open and readily available for manipulation. Access to the tubing upstream from the pump is not allowed; thus, preventing unauthorized withdrawal of the fluid, such as with a needle in the case of a controlled substance. The enclosures described in the above referenced applications are easy to use, provide protection to the reservoir and are neither bulky nor awkward to use.

There is a desire to use the enclosures discussed herein with a variety of sizes of pumps. As is recognized in the art, ambulatory pumps are expensive to produce and to purchase. Hospitals, physicians and managed care providers are not always able to purchase the pump specifically designed to associate with a given enclosure. Yet, there is an increasing need to move toward a pump/enclosure arrangement particularly where the patient is not under constant supervision by medical personnel. The adaptors and methods of the present invention are designed to provide an inexpensive alternative to the purchase of matched pump/enclosure systems.

SUMMARY OF THE INVENTION

The present invention relates generally to an adaptor to secure an infusion-type pump to an enclosure, where the enclosure is designed to house a fluid reservoir and tubing extending from the reservoir to the infusion-type pump to deliver fluid medicament to a patient. The adaptor comprises a main body having a front and a back, a pump mounting mechanism extending from the front of the body to mount the infusion-type pump to the body and a back projection extending from the back of the body sized to engage the enclosure.

More specifically, the present invention relates to an adaptor to secure an infusion-type pump to an enclosure where the adaptor preferably includes a substantially planar body having a back face, a front face, a top end, a bottom end and two lateral edges. At least two opposed guide walls project substantially perpendicularly from the front face along the two lateral edges. A support plate is positioned at the top end of the adaptor and spaced from the front face to receive a portion of the infusion-type pump. The adaptor also includes at least one securing grip along the front face of the adaptor to securably mount the infusion-type pump to the adaptor. A mounting device is provided to allow selective mounting of the adaptor to the enclosure.

The support plate preferably limits movement of one end of the pump. In one preferred aspect of this invention, the guide walls extend down substantially the entire length of the adaptor. In a second preferred aspect of the invention, the guide walls form guide bars positioned along the lateral edges of the adaptor. These further limit movement of the pump.

The grip preferably limits movement of an opposite end of the pump. The grip includes at least one L-shaped clip extending from the bottom of the adapter. The grip preferably forms an automatic locking projection extending from the front face of the support plate.

In a preferred embodiment of this invention, the back face of the adaptor includes at least one ridge sized to mate with an edge of the enclosure. A pole mounting arrangement may also be provided on the back face to enable mounting of the pump and adapter to a pole.

The invention also relates to an infusion system comprising an infusion-type pump, an enclosure sized to house a fluid reservoir and tubing extending from the fluid reservoir to the infusion-type pump, and an adaptor securing the infusion-type pump to the enclosure. Preferably the pump further comprises a control module and a pressure plate.

In another aspect of this invention, a method is provided for using an infusion system comprising the steps of mounting an infusion-type pump onto an adaptor, introducing a fluid reservoir and tubing extending from the fluid reservoir into an enclosure and securing the adaptor to the enclosure. Preferably, the pump comprises a control module and a pressure plate, and the adaptor comprises a substantially planar body having a back face and a front face, the front face having guide walls and a support plate to position an infusion-type pump to the adaptor, at least one grip to securably mount the infusion-type pump to the adaptor and a locking mechanism to selectively secure the adaptor onto the enclosure.

In a preferred method of this invention the securing step further comprises the steps of guiding the infusion-type pump onto the adaptor, positioning the pump onto a support plate and engaging a securing grip positioned on the adaptor. Preferably, the adaptor can be disengaged from the enclosure, and the enclosure and adaptor can be reused.

DETAILED DESCRIPTION OF THE PREFERRED EMBODIMENTS

The reservoir enclosure adaptor and method of the present invention allows for pumps of different sizes to be used with separate reservoir enclosure arrangements that are not specifically designed to matingly fit together during use. The adaptor connects the pump to the enclosure so as to close off the opening into the enclosure in order to protect the fluid reservoir and tubing stored within the enclosure.

Figure 1:
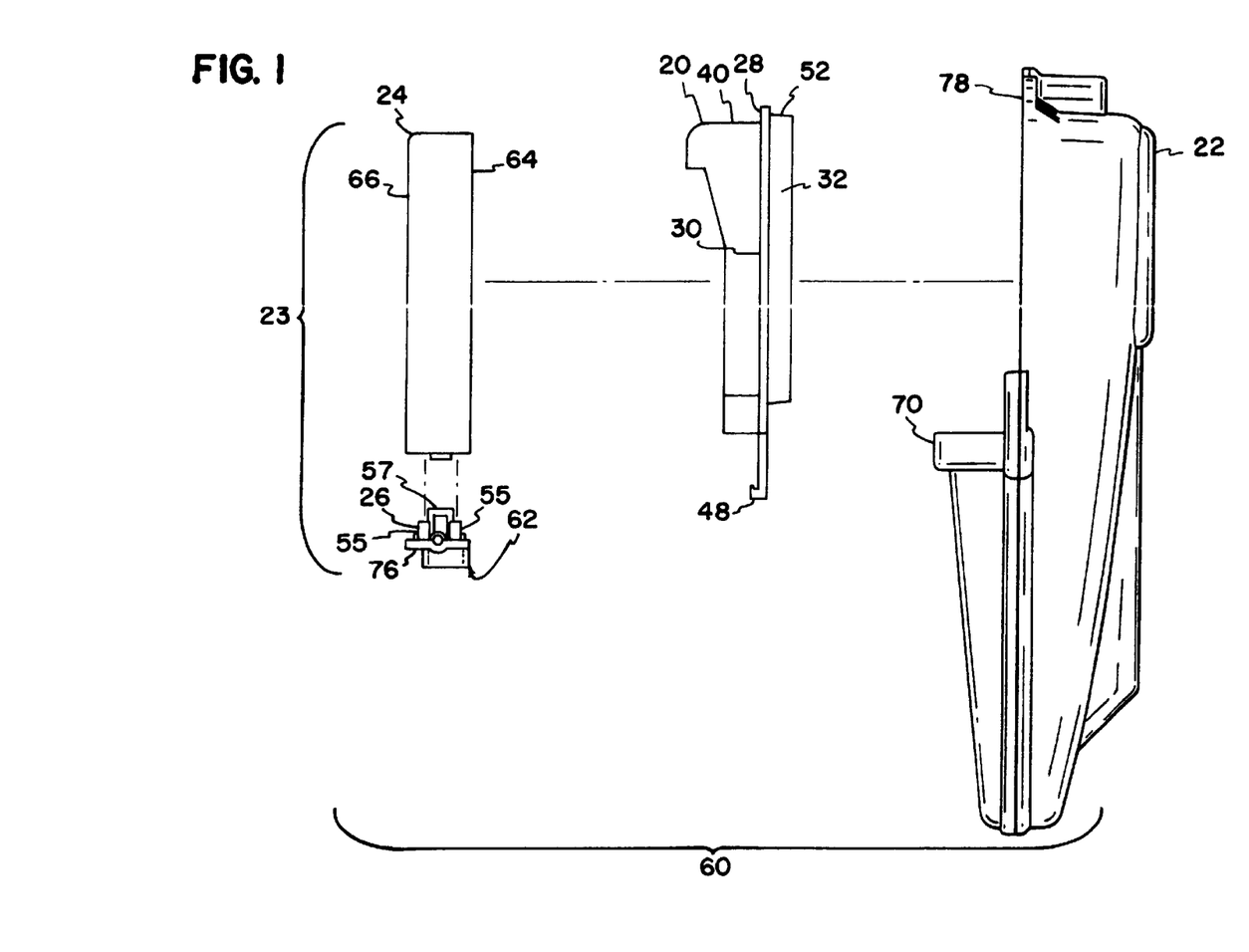
FIG. 1 is an exploded side view of a first preferred embodiment of an infusion system including an enclosure arrangement, an adaptor, and a pump, including a control module and a pressure plate.

Referring now to FIG. 1, a first embodiment of a pump adapter 20 is shown aligned to communicate with an enclosure 22. Pump adaptor 20 (hereinafter referred to as "adaptor") is used to adapt pumps of varying sizes to conform to enclosure type arrangements, such as those provided in U.S. patent application Ser. Nos. 08/145,371 and 08/388,200. Enclosure 22 is used as an enclosure arrangement designed to house a fluid reservoir and tubing thereby protecting the tubing and reservoir from damage or manipulation during use.

Figure 2:
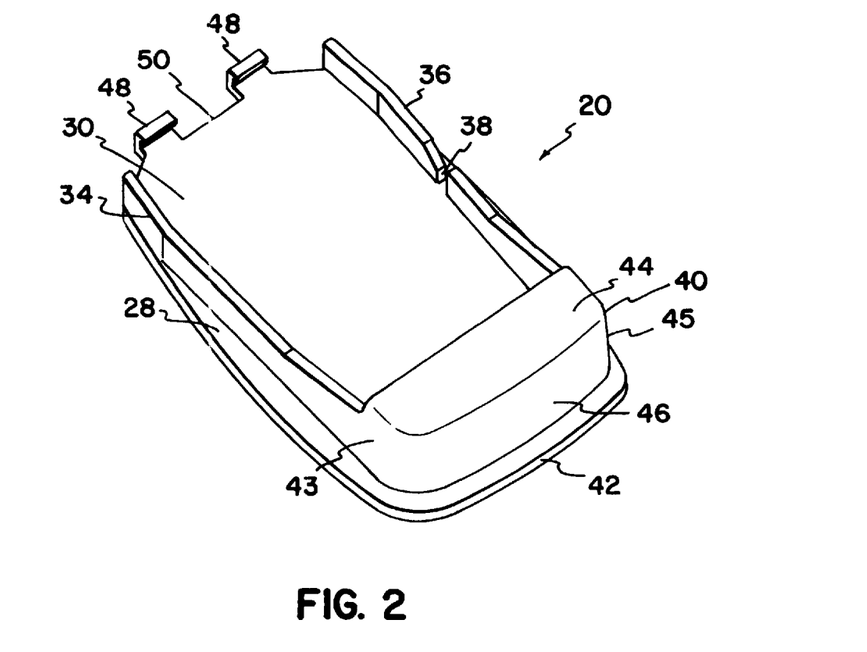
FIG. 2 is a front perspective view of the first embodiment of the adaptor shown in FIG. 1.
Figure 3:
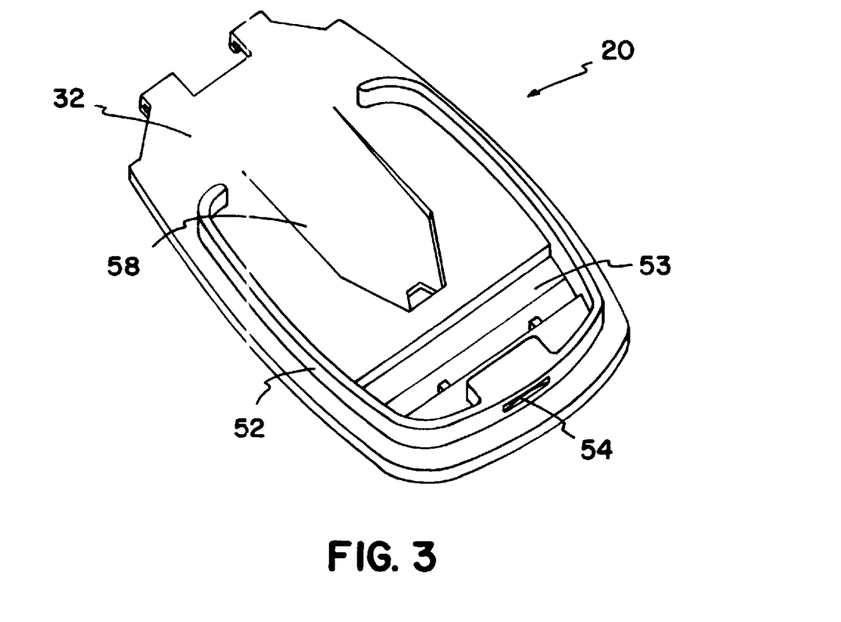
FIG. 3 is a back perspective view of the first embodiment of the adaptor shown in FIG. 1.
Figure 4:
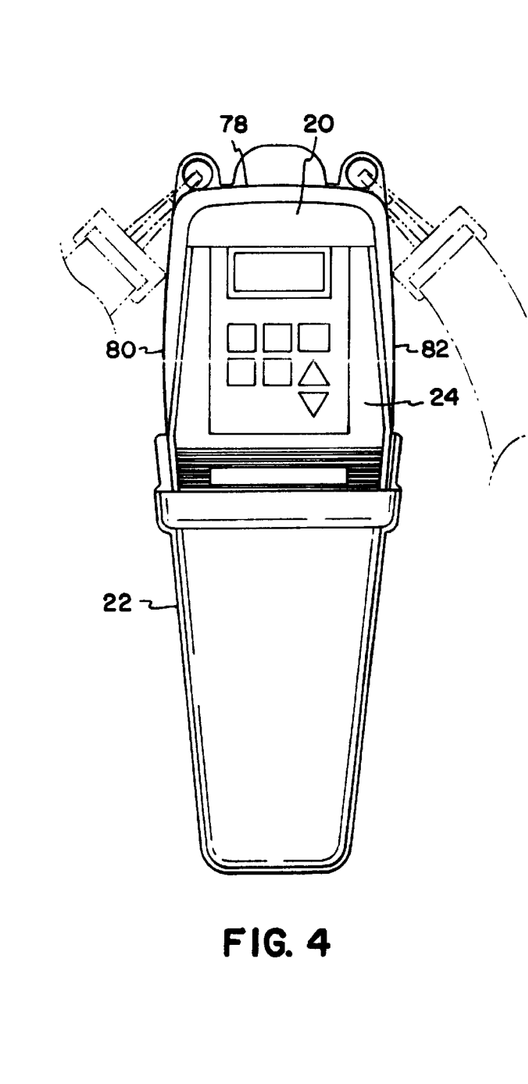
FIG. 4 is a front view of the infusion system of FIG. 1.
Figure 5:
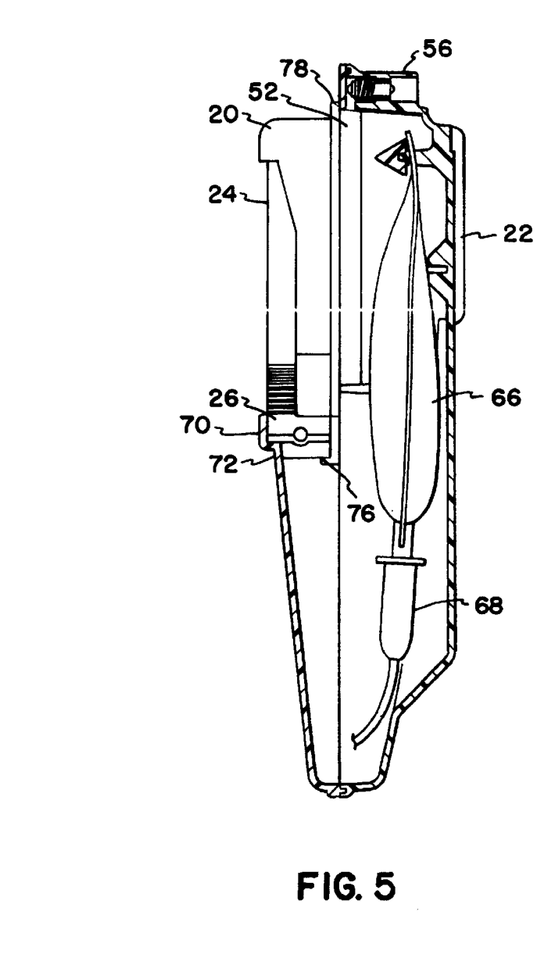
FIG. 5 is a side view of the infusion system of FIG. 1, with the enclosure arrangement shown in cross-section.

As illustrated in FIGS. 1, 4 and 5 during use, a pump 23, including a control module 24 and a detachable pressure plate 26, is mounted onto adaptor 20 and positioned onto enclosure 22. A tubing extending from the fluid reservoir to the patient is positioned between pressure plate 26 and control module 24. Tube engaging members extending from control module 24 sequentially squeeze the tubing against the pressure plate to effect pumping. Two hooks 55 and a loop 57 extend from pressure plate 26 to mount pressure plate 26 to control module 24, such as described in U.S. Pat. No. 4,559,038, for example. As a reference for the orientation of the pump, the pressure plate will be referred to in this disclosure as being positioned along the bottom portion of the pump. Referring now to FIGS. 1–3, adaptor 20 includes a substantially planar support plate 28 having a front face 30 and a back face 32. A first guide wall 34 and a second guide wall 36 extend from front face 30 in an outwardly direction, preferably at about 90° angles relative to front face 30. These guide walls serve as guides to position and hold pump 23 in place.

Other guide wall configurations are contemplated in this invention. For example, the guide walls may be formed as ridges, knobs, posts, or the like. The height of the guide wall should be sufficient to keep the pump positioned on the adaptor.

One or more discontinuities, gates or openings are provided in the guide walls 34 or 36, as necessary, to permit access to communication ports along the lateral aspects of pump 23. These communication ports include, but are not limited to, ports for power sources, communication cables, and the like. FIG. 2 illustrates a first guide wall opening 38 to form a discontinuity in the second guide wall 36. This guide wall opening can take any of a variety of forms or shapes including holes, breaks, or slots in the guide walls. The particular design of the pump will determine the location of the openings in either the first guide wall, the second guide wall, or both.

Adaptor 20 includes a top support plate 40 positioned at a top end 42 on front face 30 of support plate 28. In this embodiment, top support plate 40 is configured as a hood designed to preferably provide a cradle-like support for the top end of pump 23, that portion of the pump opposite the pressure plate function, to hold the pump in place. Thus, the combination of top support plate 40, first guide wall 34 and second guide wall 36 position the upper portion and the side portions of control module 24 in place on adaptor 20.

Top support plate 40 of FIG. 2 includes a front surface 44 and a top surface 46. In this embodiment, the sides 43,45 of top support plate 40 are formed from the extended first guide wall 34 and the extended second guide wall 36. Those skilled in the art will recognize that the guide walls do not necessarily need to communicate directly with top support plate 40; however, such an arrangement provides additional positioning and support for the control module when it is placed onto adaptor 20. In FIG. 2, the top portions of first guide wall 34 and second guide wall 36 slope upward and increase in height until they communicate with front surface 44 of top support plate 40.

Figure 1A:
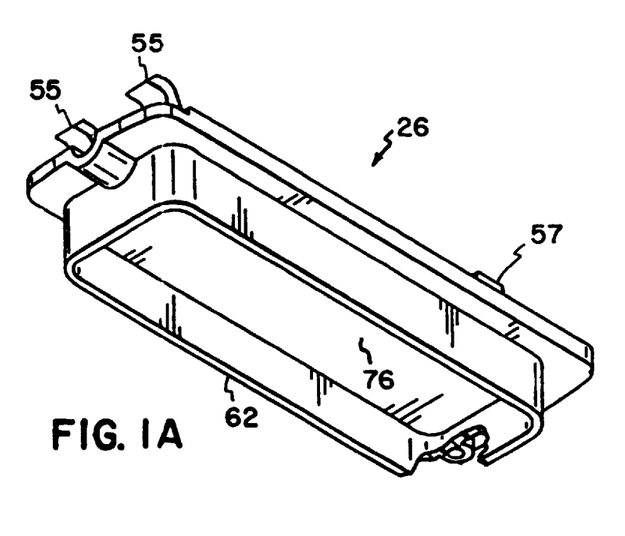
FIG. 1A shows a lower surface of the pressure plate of FIG. 1 in greater detail.

Two securing grips 48 are positioned along a bottom end 50 of support plate 28. Securing grips 48 can take any of a variety of conformations. For example, one grip may be sufficient. In the first embodiment shown, securing grips 48 form two hooked or L-shaped finger-like projections extending from and continuous with bottom end 50 of support plate 28. In this embodiment, pump 23 is slidably engaged in adaptor 20 and guided by guide walls 34 and 36 until the top end of the pump is fully supported by top support plate 40. Pump 23 is then pressed into support plate 28 such that securing grips 48 hold the pump in place on the adaptor through a grip formed between securing grips 48 and a lower lip 62 of pressure plate 26. FIG. 1A shows lower lip 62 of pressure plate 26 in greater detail. While securing grips 48 of FIGS. 2 and 3 comprise two securing grips positioned to the left and right of the center longitudinal plane of adaptor 20, any of a variety of grips, latches, locks or hooks can be used to keep the pump in place on the adaptor.

FIG. 3 illustrates back face 32 of adaptor 20. Back face 32 of adaptor 20 includes a ridge 52 for cooperating with enclosure 22 to mount pump 23, including control module 24 and pressure plate 26, to enclosure 22. Ridge 52 need not be generally rectangular (with slightly convexly curved sides) in outer perimeter as shown in FIG. 3. However, ridge 52 needs sufficient structure to cooperate with enclosure 22 to permit the secure mounting of adaptor 20 and pump 23 to enclosure 22. Also, preventing needle access to the fluid reservoir is accomplished by having ridge 52 extend fully around back face 32 as shown in the Figures. Ridge 52 fits within an inner perimeter defined by the opening into enclosure 22.

A lock slot 54 is provided at or close to top end 42 of back face 32 of support plate 28. Lock slot 54 is located in ridge 52 in the embodiment illustrated in FIG. 3. Lock slot 54 is designed to cooperate with a latch structure 56 as shown on the side view of enclosure 22 of FIG. 5. In a preferred embodiment, enclosure 22 includes a rotatable latch arrangement with a spring loaded two position latch. The latch arrangement is positionable in either one of two positions, locked or unlocked as the latch position is rotated 90° to change from one position to another. This preferred latch structure 56 with lock slot 54 is discussed in detail in U.S. patent application Ser. Nos. 08/145,371 and 08/388,200. Rotation of the latch releases or locks adaptor 20 to enclosure 22. Other latch arrangements are possible for selectively holding the adaptor 20 to the enclosure 22. Any appropriately configured structure for selectively and releasably gripping, holding or trapping adaptor 20 to enclosure 22 is useable.

Openings, such as opening 53, are provided along support plate 28 to facilitate manufacture from molded plastics. Back face 32 of adaptor 20 also includes a mounting arrangement 58 for mounting adaptor 20 to a plate of a pole mounting system. Alternatively, back face 32 could include other mounting structures for mounting adaptor 20 to another object, such as a pole, a bed head board, or a belt to be worn by the patient. Thus, the combination of adaptor 20 and pump can be separately mounted without enclosure 22.

Referring again to FIG. 1, a preferred infusion system 60 includes pump 23 with control module 24 and pressure plate 26, adaptor 20, and enclosure 22. In use, pump 23 is inserted onto adaptor 20, guided into position using first guide wall 34, second guide wall 36 and top support plate 40. Securing grips 48 are positioned over lower lip 62.

With pump 23 in place on adaptor 20, the adaptor/pump combination can be mounted onto enclosure 22. As illustrated in FIG. 5, enclosure 22 is first equipped with a fluid reservoir 66 housing a suitable fluid medicament and outfitted with the appropriate fluid conduit arrangement 68. Fluid conduit arrangement 68 is in fluid communication with tubing passing through and across pressure plate 26. Adaptor 20 is positioned within the interior of enclosure 22 adjacent front retaining lip 70, top edge portion 78 and side edge portions 80 and 82 (see FIG. 5). As seen by the side view in FIG. 5, retaining lip 70 and pump support surface 72 forms a trough-like structure just wide enough to snugly accommodate the pump. As a preferred method for stably positioning pump 23 on pump support surface 72, pressure plate 26 is provided with a nonplanar under surface 76. The nonplanar under surface is designed to engageably mate with the contours of the interior portions of the trough and pump support surface 72.

Adaptor 20 is further maintained in position on enclosure 22 through the engagement of back ridge 52 on back face 32 of adaptor 20 with top edge portion 78 and side edge portions 80 and 82 of the enclosure, as illustrated in FIGS. 4 and 5. Once adaptor 20 is in position and aligned with enclosure 22, lock slot 54 on adaptor 20 is engaged with latch structure 56 on enclosure 22.

Once it is desired to access the enclosure chamber to remove the fluid reservoir 66 or the fluid conduit arrangement 68, such as when reservoir 66 is emptied or needs to be changed, latch structure 56 on enclosure 22 is disengaged to release the latch from lock slot 54 to release top end 42 of support plate 40 of adaptor 20. Adaptor 20, with the pump, is then separable from enclosure 22. To release pump 23 from adaptor 20, pump 23 is pulled in a direction generally parallel to front face 30 and away from top support plate 40. Flexibility provided in securing grips 48 allows pump 23 to be moved sufficiently relative to adaptor 20 that the top end of pump 23 clears top support plate 40 such that pump 23 can be separated from adaptor 20.

Adaptor 20 can be made from any of a variety of materials known to those skilled in the art. Adaptor 20 is preferably made from a light weight, strong polymeric material, preferably molded plastic including but not limited to polycarbonate, polyvinyl chloride (PVC), and the like. The adaptor may be prepared as a single, molded piece or as one or more pieces adhesively bonded, heat bonded or ultrasonically welded, for example, together during assembly using tongue and groove joints, or the like. Those skilled in the art will readily appreciate the cost, manufacturing and production advantages to single or multiple pieced adaptors and will be able to select the particular manufacturing process best fitted to their needs.

Figure 6:
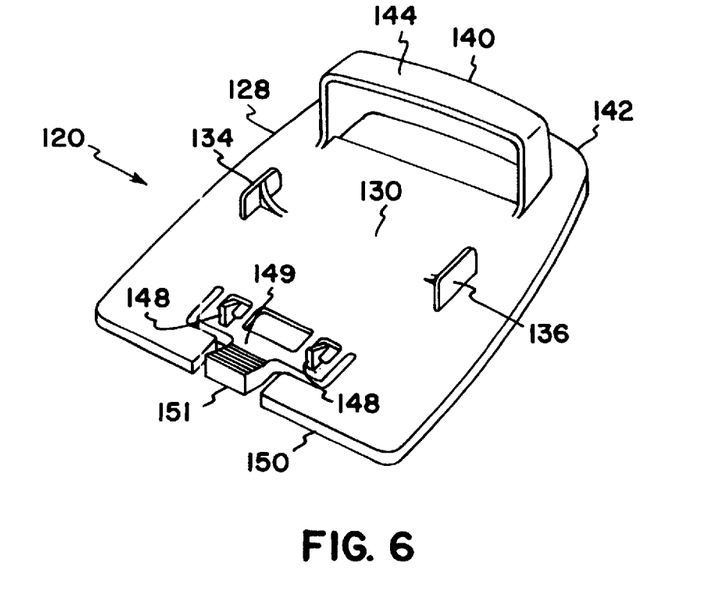
FIG. 6 is a front perspective view of a second embodiment of an adaptor according to the present invention.
Figure 7:
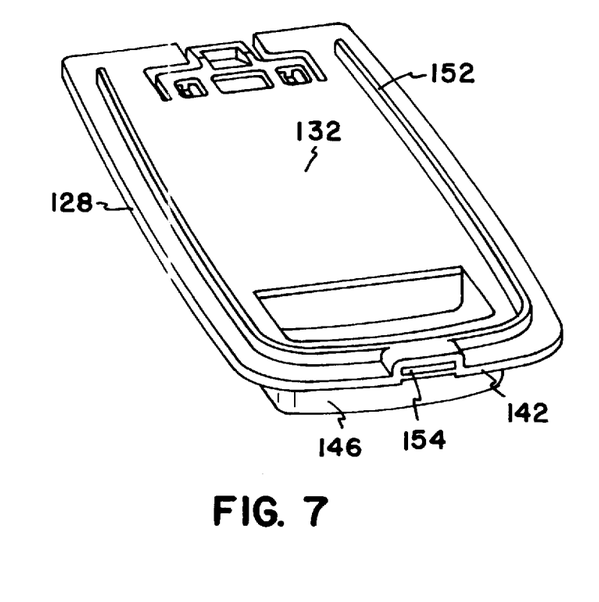
FIG. 7 is a back perspective view of the second embodiment of the adaptor shown in FIG. 6.

Referring now to FIGS. 6 and 7, a second embodiment of an adaptor 120 is shown. Adaptor 120 is preferably includes a support plate 128 having a front face 130 and a back face 132. In this embodiment, a first guide wall 134 and a second guide wall 136 extend from front face 130 in an outwardly direction, preferably at about 90° angles relative to front face 130. These guide walls serve as guides to position the pump in place.

The second embodiment illustrated in FIGS. 6 and 7 includes a top support plate 140 positioned at a top end 142 of support plate 128. In this embodiment the top support plate 140 is again configured as a hood designed to preferably provide a cradle-like support for the top end of the control module to hold it in place. Thus, the combination of the top support plate 140, the first guide wall 134 and the second guide wall 136 align the upper portion and the side portions of control module 24 on adaptor 120.

Top support plate 140 of FIG. 6 includes a front surface 144 and top surface 146. In this embodiment, top support plate 140 is formed as a hood that attaches to support plate 128. The hood can be formed as part of a mold or as one or more pieces adhesively bonded, heat bonded or ultrasonically welded to support plate 128.

Pressure-locking securing grips 148 are positioned along the bottom end 150 of support plate 128. These pressure-locking securing grips 148 can take any of a variety of conformations. In the embodiment of FIGS. 6 and 7, the securing grips form two hooked finger-like projections extending from a release plate 149. The release plate is preferably formed as a three-sided cut out associated with the support plate 128; however, it will be understood that a variety of release plate configurations will equally function in this embodiment. A release bar 151 forms an end of release plate and preferably includes slip-resistant ridges 153.

In this embodiment pump 23 is slidably engaged in the adaptor 120 and guided by guide walls 134 and 136 until the top end of the pump is fully supported by top support plate 140. Pressure applied to the lower portion of the pump toward adaptor 120 secures the pump onto the adaptor via the pressure-locking securing grips 148. The pump is released from adaptor 120 by pressing on release bar 151 which releases the pressure-locking securing grips from the pump.

FIG. 7 illustrates back face 132 of adaptor 120. Like the first embodiment, back face 132 of adaptor 120 includes a ridge 152 for cooperating with enclosure 22 to mount pump 23, including control module 24 and pressure plate 26, to enclosure 22. Ridge 152 needs sufficient structure to cooperate with enclosure 22 to permit the secure mounting of the pump to the enclosure 22. Ridge 152 fits within an inner perimeter defined by the opening into enclosure 22.

A lock slot 154 is provided at or close to top end 142 of back face 132 of support plate 128. Lock slot 154 is designed to cooperate with latch structure 56 of enclosure 22 of FIG.

4. Rotation of the latch on enclosure 22 releases or locks adaptor 120 to the enclosure.

Although not shown, it is also contemplated that the back face 132 of adaptor 120 can also include a mounting arrangement such as the mounting arrangement 58 shown and described on FIG. 3 for mounting adaptor 120 to a plate of a pole mounting system. Like adaptor 20, adaptor 120 can be made from any of a variety of materials known to those skilled in the art.

A preferred infusion system using adaptor 120 includes pump 23 with control module 24 and pressure plate 26, adaptor 120, and enclosure 22. In this preferred embodiment of the infusion system, pump 23 mounts to adaptor 120 in a similar manner as adaptor 20. Pressure-locking securing grips 148 are positioned onto lower lip 62 using pressure directed from the bottom portion of the pump toward securing grips 148 on adaptor 120. With the pump in place on adaptor 120, the adaptor/pump combination is mounted onto enclosure 22 as described in the above discussion related to the first embodiment.

Like adaptor 20, adaptor 120 is further maintained in position on enclosure 22 through the engagement of back surface ridge 152 on back face 132 of adaptor 120 with top edge portion 78 and side edge portions 80 and 82 of the enclosure, as demonstrated for adaptor 20 illustrated in FIGS. 4 and 5. Once adaptor 120 is in position and aligned with enclosure 22, lock slot 154 on the adaptor is engaged with latch structure 56 on enclosure 22.

When it is desired to access the enclosure chamber to remove fluid reservoir 66 or fluid conduit arrangement 68, such as when reservoir 66 is emptied or changed, latch structure 56 on enclosure 22 is disengaged to release the latch from lock slot 154 to release the top end of support plate 142 of adaptor 120. Adaptor 120 with the pump is then separable from enclosure 22. Pressure applied to release bar 151 releases the pressure-locking securing grips 148 holding the pump to the adaptor 120.

While the present invention has been described in connection with the preferred embodiments thereof, it will be understood that many modifications will be readily apparent to those skilled in the art, and this application is intended to cover any adaptations or variations thereof. It is manifestly intended that this invention be limited only by the claims and equivalents thereof.

What is claimed is:

1. An adaptor to secure an infusion-type pump to an enclosure, the pump having an outer housing and a pump mechanism including tube engaging members for moving fluid through a tubing, wherein the enclosure is designed to house a fluid reservoir and the tubing extending from the reservoir to the infusion-type pump to deliver fluid medicament to a patient, the adaptor comprising:

a body having a front and a back, the front facing in an opposite direction to the back;

a pump mounting mechanism extending from the front of the body to mount the outer housing of the infusion-type pump to the body; and a back projection extending from the back of the body sized to removably engage the enclosure.

2. An adaptor for use with an infusion-type pump and an enclosure comprising:

a body having a back face, a front face, a top end, a bottom end and two lateral edges;

at least two opposed guide walls positioned substantially perpendicular to and extending from the front face and positioned along the two lateral edges;

a support plate positioned at the top end of the adaptor and spaced from the front face to receive a portion of the infusion-type pump;

at least one securing grip at the bottom end of the adaptor to securably mount the infusion-type pump to the adaptor; and a mounting device to allow selective mounting of the adaptor to the enclosure.

3. The adaptor of claim 2, wherein the support plate limits movement in two directions.

4. The adaptor of claim 2, wherein the guide walls extend down substantially the entire length of the adaptor.

5. The adaptor of claim 2, wherein the guide walls form guide bars positioned along the lateral edges of the adaptor.

6. The adaptor of claim 2, wherein the back face of the adaptor includes a pole mounting arrangement.

7. The adaptor of claim 2, wherein the back face includes at least one ridge sized for receipt in the enclosure.

8. The adaptor of claim 2, wherein the grip is an L-shaped clip.

9. The adaptor of claim 2, further comprising a second securing grip at the bottom end of the adaptor.

10. The adaptor of claim 9, wherein the securing grips extend from the bottom of the adaptor.

11. The adaptor of claim 2, wherein the mounting device includes the body defining a projection receiving slot.

12. The adaptor of claim 2, wherein a release bar extends from the front face of the support plate and wherein pressure applied to the release bar repositions the securing grip.

13. An infusion system comprising:

an infusion-type pump having an outer housing including a keyboard and a pump mechanism including tube engaging members for moving fluid through a tubing;

a substantially rigid enclosure sized to house a fluid reservoir and the tubing extending from the fluid reservoir to the infusion-type pump, the enclosure defining an opening, and an adaptor securing the outer housing of the infusion-type pump to the enclosure at the opening so as to close the opening, wherein the keyboard is exposed for access by an operator when the enclosure receives the fluid reservoir and the tubing and the adapter secures the pump to the enclosure.

14. The system of claim 13, wherein the pump further comprises a control module and a pressure plate.

15. A method for assembling an infusion system comprising the steps of:

mounting an outer housing of an infusion-type pump onto a front of an adaptor;

placing a fluid reservoir and a tubing extending from the fluid reservoir through an opening into an enclosure wherein the tubing extends from the fluid reservoir to the infusion-type pump; and after placing the fluid reservoir and the tubing into the enclosure, securing a back of the adaptor to the enclosure to close the opening, the front of the adaptor facing in an opposite direction to the back.

16. The method of claim 15, wherein the pump comprises a control module and a pressure plate.

17. The method of claim 15, wherein the adaptor comprises: a substantially planar plate having a back face and a front face, the front face having guide walls and a support plate to position an infusion-type pump to the adaptor, at least one grip to securably mount the infusion-type pump to the adaptor and a locking mechanism to reversibly position the adaptor onto the enclosure.

18. The method of claim 15, wherein the securing step further comprises the steps of guiding the infusion-type pump onto the adaptor, positioning a portion of the pump under a support plate of the adaptor and engaging the pump with securing grips positioned on the adaptor.

19. The method of claim 15, further comprising the step of unsecuring the adaptor from the enclosure.

20. A method for securing a pump to an enclosure designed to house a fluid reservoir and a tubing extending from the fluid reservoir to the infusion-type pump, the pump having an outer housing and a pump mechanism including tube engaging members for moving fluid through the tubing, comprising the steps of:

securing the outer housing of the infusion-type pump to an adaptor;

mating the adaptor onto the enclosure wherein the enclosure houses a fluid reservoir and the tubing extending from the fluid reservoir to the infusion-type pump; and locking the adaptor to the enclosure to secure the adaptor onto the enclosure.

21. The method of claim 20, further comprising the step of unlocking the adaptor from the enclosure.

* * * * *